(12) United States Patent
Knobloch

(10) Patent No.: US 9,999,725 B2
(45) Date of Patent: Jun. 19, 2018

(54) SAFETY NEEDLE DEVICE, PARTICULARLY FOR THE PUNCTURE OF A PORT IMPLANTED SUBCUTANEOUSLY IN A HUMAN OR ANIMAL BODY

(71) Applicant: PFM MEDICAL AG, Cologne (DE)

(72) Inventor: Helmut Knobloch, Kreuzau (DE)

(73) Assignee: PFM MEDICAL AG, Cologne (DE)

( * ) Notice: Subject to any disclaimer, the term of this patent is extended or adjusted under 35 U.S.C. 154(b) by 758 days.

(21) Appl. No.: 14/387,355

(22) PCT Filed: Mar. 20, 2013

(86) PCT No.: PCT/EP2013/000845
§ 371 (c)(1),
(2) Date: Sep. 23, 2014

(87) PCT Pub. No.: WO2013/139476
PCT Pub. Date: Sep. 26, 2013

(65) Prior Publication Data
US 2015/0314067 A1    Nov. 5, 2015

(30) Foreign Application Priority Data
Mar. 23, 2012    (DE) .................. 10 2012 102 519

(51) Int. Cl.
*A61M 5/00*    (2006.01)
*A61M 5/162*    (2006.01)
(Continued)

(52) U.S. Cl.
CPC ........ *A61M 5/1626* (2013.01); *A61M 5/3275* (2013.01); *A61M 5/3273* (2013.01);
(Continued)

(58) Field of Classification Search
CPC ........ A61M 5/3273; A61M 2005/1581; A61M 2005/3226; A61M 5/1626; A61M 5/3275
See application file for complete search history.

(56) References Cited

U.S. PATENT DOCUMENTS 6,997,902 B2    2/2006    Thorne et al.
7,097,637 B2    8/2006    Triplett et al.
(Continued)

FOREIGN PATENT DOCUMENTS

CN    1878584    12/2006
EP    1256355    11/2002
(Continued)

OTHER PUBLICATIONS

International Search Report from corresponding PCT Appln. No. PCT/EP2013/000845 dated Jun. 6, 2013.

*Primary Examiner* — Rebecca E Eisenberg
(74) *Attorney, Agent, or Firm* — Grossman, Tucker, Perreault & Pfleger, PLLC

(57) ABSTRACT

The invention relates to a safety needle device, particularly for the puncture of a port implanted subcutaneously in a human or animal body, comprising a first housing; a hollow needle, wherein the needle has a first sub-section and a second sub-section, and the first sub-section extends along a puncture axis, which runs at a right angle to the surface of the human or animal body, and the second sub-section of the needle being arranged at a right angle to the first sub-section, substantially parallel to the surface of the human or animal body, wherein the hollow needle is or can be connected to the first housing, particularly in the region of the second sub-section; a cover comprising a through-hole for receiving the first sub-section of the needle, wherein the cover can be moved from a first position into a second position relative to the first housing, wherein the movement occurs substantially along the puncture axis; and an at least partially flexible
(Continued)

limiting element for limiting the relative movement between the first housing and the cover in the second position; wherein the device is characterized in that the cover has, on the surface facing away from the human or animal body, a guide sleeve for the first sub-section of the needle.

29 Claims, 10 Drawing Sheets

(51) Int. Cl.
 *A61M 5/32* (2006.01)
 *A61M 5/158* (2006.01)
(52) U.S. Cl.
 CPC ............... *A61M 2005/1581* (2013.01); *A61M 2005/3226* (2013.01)

(56) References Cited

U.S. PATENT DOCUMENTS

| | | | |
|---|---|---|---|
| 7,867,201 B2 | 1/2011 | Huet | |
| 2003/0114797 A1 | 6/2003 | Vaillancourt et al. | |
| 2005/0107748 A1* | 5/2005 | Thorne | A61M 5/158 604/263 |
| 2008/0262434 A1 | 10/2008 | Vaillancourt | |
| 2009/0163875 A1* | 6/2009 | Hiraoka | A61M 5/158 604/192 |
| 2012/0065587 A1* | 3/2012 | Barron | A61M 5/158 604/110 |

FOREIGN PATENT DOCUMENTS

| | | |
|---|---|---|
| EP | 1011759 | 11/2005 |
| EP | 1562659 | 6/2008 |
| EP | 2016964 | 1/2009 |
| FR | 2941867 | 8/2010 |
| JP | 2008-554 | 1/2008 |
| WO | 02/096493 | 12/2002 |
| WO | 03/074112 | 9/2003 |
| WO | 20071137339 | 12/2007 |

* cited by examiner

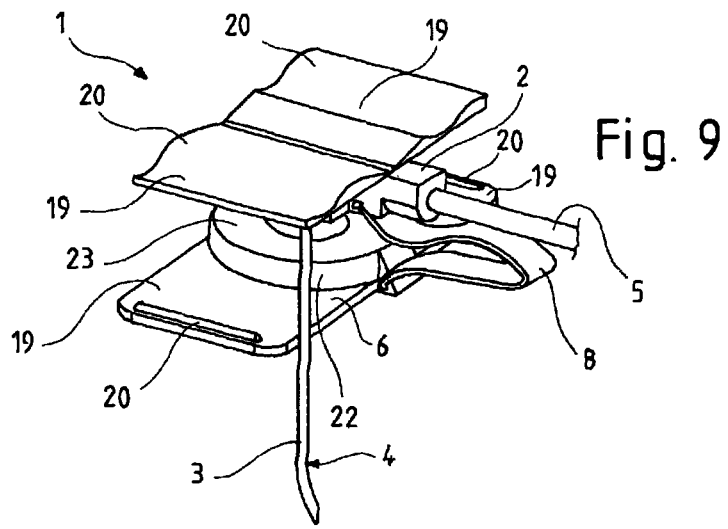
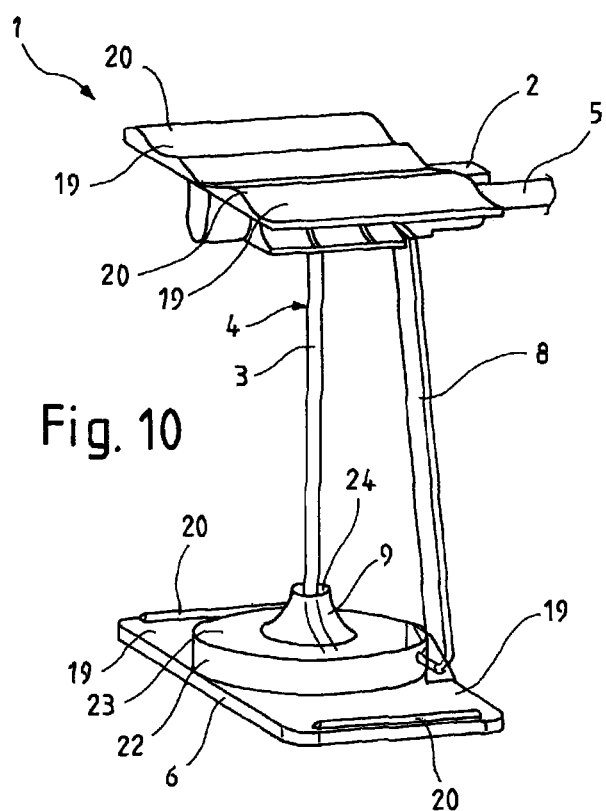

SAFETY NEEDLE DEVICE, PARTICULARLY FOR THE PUNCTURE OF A PORT IMPLANTED SUBCUTANEOUSLY IN A HUMAN OR ANIMAL BODY

CROSS-REFERENCE TO RELATED APPLICATION

This is the U.S. National Phase Application under 35 U.S.C. § 371 of International Patent Application No. PCT/EP2013/000845 filed Mar. 20, 2013, which claims the benefit of German Patent Application No. 10 2012 102 519.3 filed on Mar. 23, 2012, both of which are incorporated by reference herein.

FIELD OF THE INVENTION

The present invention relates to a safety needle device, particularly for the puncture of a port implanted subcutaneously in a human or animal body, comprising a first housing; a hollow needle, wherein the needle has a first sub-section and a second sub-section, and the first sub-section extends along a puncture axis, which runs at a right angle to the surface of the human or animal body, and the second sub-section of the needle being arranged at a right angle to the first sub-section, substantially in parallel to the surface of the human or animal body, wherein the hollow needle is or can be connected to the first housing, particularly in the region of the second sub-section; the cover comprising a through-hole for receiving the first sub-section of the needle, wherein the cover can be moved from a first position into a second position relative to the first housing, wherein the movement occurs substantially along the puncture axis; and an at least partially flexible limiting element for limiting the relative movement between the first housing and the cover in the second position.

BACKGROUND

Such safety needle devices are used for the application of medicaments, for example in the field of oncology. In the context of a therapy medicaments have to be applied frequently and over a longer period of time. To achieve this painless and with minimal tissue damage for example, a port is attached to a port catheter subcutaneously on the chest of the patient. A tube of the port catheter connects the port with the vein close to the heart in order to bring the medicament quickly into the bloodstream. In this case the port catheter has a chamber which is closed by a silicon membrane. The safety needle device is pierced through the tissue of the human or animal body and the membrane until the needle tip of the safety needle device reaches the bottom of the port. The opening of the needle tip is now located in the hollow chamber of the port and the medicament can be directed into the patient's body. In order to prevent a usually pain causing movement of the needle, the needle housing is attached to the skin with a patch. Upon removal of the needle, the port has to be kept down, since it is otherwise lifted due to the friction between the needle and the membrane which causes pain due to the connection with the tissue of the human or animal body. The risk of injury is very high after the removal of the safety needle device. To reduce needlestick injuries and associated risks of infection, at least the sharp needle tip should be securely covered against contact. The manual placing of the cover used for transportation is not suitable to protect the medical personnel which removes the needle from the port against injuries, in particular because a risk for injury exists when manually placing the cover used for transportation.

EP 1 562 659 B1 discloses a safety needle device, in particular for puncturing of a subcutaneously implanted port in a human or animal body. The device comprises a base plate, a needle carrier plate and a cover plate, wherein the base plate and the needle carrier plate are each hingedly connected to the cover plate. An angled needle is provided for the needle carrier plate, which has a distal, perforated leg and a proximal leg for the injection of a medicament. The base plate comprises a through-hole, through which the proximal leg of the needle can be passed. Furthermore, the cover plate also has a through-hole for the distal leg of the needle. In the first state the distal leg of the needle is passed through the through-hole in the base plate and through the through-hole in the cover plate. In this state the base plate and the needle carrier plate form an upper part of the device whereas the cover plate forms a lower part of the device, wherein the upper part and the lower part are located on each other. In this state the distal leg of a needle protrudes downwardly from the device and can be inserted into the subcutaneously implanted port. For this purpose the upper part of the device comprises two wings which can be folded into a vertical position in order to better insert the device into the port. During the use of the disclosed safety needle device the device is being fixed on the surface of the human or animal body by means of plaster. For removal of the safety needle device, the lower cover plate also comprises two wings, with which the cover plate can be fixed simultaneously with the port relatively to the human or animal body during removal of the safety needle device. To pull out the distal leg of the needle from a port, the wings at the upper part of the device are positioned vertically and the operator can move the upper part to the top with the other hand while the lower part is fixed relative to the human or animal body. Once the distal leg of the needle has been pulled out of the human or animal body and the needle tip exits the trough-hole in the cover plate, thereby the distal leg moves, caused by a pretention to a pincushion provided at the cover plate, protecting the needle tip from contact. Due to the pretension an undesirable lateral movement of the needle tip may be caused, before the distal leg of the needle has left the port catheter or the human or animal body, respectively.

WO 03/074112 A1 discloses a Huber needle-assembly with a safety mechanism. This device comprises a housing with a curved through-hole for a feed line. At the end of the curved through-hole the needle is arranged for the puncture of a human or animal body in a subcutaneously implanted port. Further a protective cover is arranged within the curved through-hole which pushes a lever over the needle to protect it from contact after the actuation. Prior to the removal of the device from the port the lever is operated and during removal of the needle of the port the protective cover automatically slides over the needle so that the operating personnel cannot injure themselves on the needle tip. A disadvantage of this device is the high structural shape which is particularly uncomfortable for long term applications of several hours or days for the patient.

EP 2 016 964 A1 discloses a safety needle device with a cover plate and a housing. The device further comprises a curved needle, whose distal end emerges from a through-hole and a cover plate in the first state and whose proximal end is arranged within the first housing in the first state. The cover plate and the housing of the device are arranged adjacent to each other in the first state. Furthermore, the device comprises a protective cover which is attached to the cover plate in the region of the through-hole of the distal end of the needle and extends into the housing while surrounding the curved needle shaft. When removing the distal end of the needle from a port, the housing is moved vertically from the cover plate. At the same time, the entire needle shaft is surrounded by the protective cover, whose end moves within a housing. Once the needle has been completely removed from the port, the needles tip is moved in such a way that it cannot inadvertently come out again through the trough-hole of the cover plate. A disadvantage of this device is that the removal of the needle from the port depends only on the skill of the operator and can cause pain for the patient when pulling out the needle in an angular direction.

EP 1 256 355 B1 discloses a safety guard adapted for the use with a needle device, comprising a main body, a pair of butterfly wings extending from the main body to the outside and a needle, which preferably extends at an angle perpendicularly from one end of the main body and further comprising an elongated substantially hollow shield, whereas said shield has open ends and an elongated slot extending between the open ends; a string which is connected with the device, so that slot and needle are substantially parallel to each other, and a fixing means which is adapted to arrange the shield in a first position substantially in parallel to the main body and to enable the shield to be rotated by a spring force to a second position e to surround and/or enclose the needle.

FR 2941867 describes a safety needle device, in particular for puncturing of a in a human or animal body subcutaneously implanted port comprising a cover plate, a needle and a housing. The cover plate has a through-hole for the needle which is attached to the housing. A collapsible sleeve is arranged between the housing and the cover plate. In a first state the needle tip protrudes through the through-hole in the cover plate and can be inserted into the port. In this state the sleeve between the cover plate and the housing is arranged folded up. When removing the needle from the port, the cover plate is fixed relatively to the human or animal body and the housing is removed from the cover plate, whereby simultaneously deploying the sleeve. In a second state the needle is completely removed from the port and is arranged between the cover plate and the housing within the deployed sleeve in a protected way. In order to prevent a needle tip from exiting the trough-hole of the cover plate again the needle tip moves to a pincushion arranged on the cover plate after removal from the port. Due to the pretension of the needle for a movement on the pincushion and the free movement between cover plate and the housing during removal of the needle, it is not guaranteed that the needle is pulled out perpendicularly to the surface of the human or animal body from the port, which leads to the previously mentioned disadvantages.

U.S. Pat. No. 7,097,367 B2 discloses a safety needle device, in particular for puncturing a subcutaneously implanted port in a human or animal body. The device comprises a cover plate, a needle, a two-part foldable housing and guiding means, which are arranged between the cover plate and the housing. In a first state the needle tip extends through a through-hole in the cover plate downwards out of the device and can be inserted into a subcutaneously implanted port. In this state the housing has an elongated shape. When the needle is removed from the port, the two-part housing is pushed together by the guiding means. An advantage of this embodiment is that the movement of the needle is guided relative to the port and human or animal body. A disadvantage of this embodiment is the very complex structure of the housing and the guiding means between the cover plate and the housing.

WO 2007/137339 A1 discloses another embodiment of the safety needle device in particular for the puncture of a in a human or animal body subcutaneously implanted port. The device comprises a cover plate with a through-hole for a needle which is insertable into the port. The device further comprises to wings which are each formed in two parts and wherein one part is guided movably in relation to another part. In a first state of the device the wings are each folded onto the cover plate and are arranged substantially in parallel to the surface of the human or animal body, and the needle extends through the through-hole in the cover plate out downwards and is insertable into a port. For removal of the needle from the port the wings are at first folded together vertically and are arranged adjacent to each other. Subsequently the relatively movable parts of the wings are removed from the surface of the human or animal body in a right angle, causing the needle to be removed from the port. After the removal, the needle is arranged in a cavity between the two wings and protected against contact. A disadvantage of this device is the complex structure, in particular the two-part wing and the guiding of the wing parts to each other.

EP 1 011 759 B1 discloses a safety apparatus for sheathing a medical needle, comprising a hollow bore cannula securely affixed in a hub and having at least one sharpened tip to form the medical needle; a molded part hingeably joined to said hub, the moulded part comprising an elongated sheath which comprises a plurality of serially interconnected substantially rigid segments each of which is interconnected to at least one adjacent segment by a hinge, each of the sheath segments comprising an open office orifice through which the cannula passes, and a channel in which the cannula is disposed when the sheath is linearly extended, the sheath and the hinges being disposed to permit folding of the sheath about the hub in a first state to permit usable access to the sharpened tip in a medical procedure and extending of the sheath to a substantially planar disposition along the cannula in which the cannula is disposed along the channel, extension of the sheath involving rotation of each sheath segment which has an orifice formed in it for the cannula about an axis which contains the orifice, the sheath including at least one latching member which catches and securely affixes the cannula to the sheath, the sheath and the cannula, in combination, forming a substantially rigid body which protectively encloses said sharpened tip and dies access thereto.

A disadvantage of the device is on the one hand the complex design of the protection device and on the other hand the high construction of the device in the first state. Furthermore, the safety device does not unfold independently, but must be operated by the operator upon removal of the needle from the human or animal body.

WO 02/096493 A1 describes a safety needle device having a first housing, a second housing, a needle and a foldable arranged protective element for the shaft of the needle between the first and the second housing. When the needle is removed from the human or animal body, the first housing is removed from the second housing, thereby unfolding the foldable protective element which then surrounds the shaft of the needle. After the needle has been removed from the human or animal body, the needle tip is arranged within the second housing and protected from contact. A disadvantage of this device is especially the high construction, whereby the device is not suitable for long term applications because the device would be disturbing for the patient.

EP 1 430 921 A1 discloses a safety needle device, in particular for puncturing of a in a human or animal body subcutaneously implanted port comprising a first housing and a second housing, a needle and a flexible sleeve arranged between the first and the second housing. In a first state the first housing and the second housing are arranged adjacent to each other and are fixed relatively to each other. In this state the needle tip protrudes from the second housing and can be inserted into a port. The protective sleeve is disposed within a cavity in the first housing. To remove the needle from the port, the locking between a first housing and the second housing is released and the second housing is fixed by the operator relatively to the human or animal body, for example by sticking. Subsequently the needle is removed from the human or animal body, which unfolds the protection sleeve arranged between the first housing and the second housing. In a second state the needle is completely pulled out of the human or animal body, wherein the needle tip is disposed within the second housing and the shaft of the needle is surrounded by the protection sleeve. The disadvantage of this device is particularly the construction height, so that the device is not suitable for long term use on patients.

US 2008/0262434 A1 discloses another safety needle device, in particular for puncturing of a in a human or animal body subcutaneously implanted port. The safety needle device comprises an upper housing to which a supply line is connectable and in which a hollow needle with a corresponding holder is arranged. The holder for the needle and the hollow needle are aligned perpendicular to the surface of the human or animal body. The device further includes a lower cover element with a through-hole for the hollow needle and a closing device for the through-hole to close the through-hole after the hollow needle has been pulled out of the human or animal body and the through-hole in the cover plate. Between the upper housing and the lower cover plate a conical protection sleeve is arranged, which surrounds the needle after removal from the human or animal body. The conical protection sleeve consists of a resistant plastic film. When removing the hollow needle from the human or animal body, the cover plate is fixed relatively to the human or animal body, for example by sticking. Subsequently the upper housing is moved relatively to the lower cover plate and thus the hollow needle is removed from the human or animal body. The conical protection sleeve has to be stretched for the complete removal of the hollow needle from the human or animal body. This has the advantage that the hollow needle is pushed through the stretched protection sleeve against the lower cover plate and is thus fixed, after the through-hole of the lower cover plate has been closed by the locking means. A disadvantage of the device is that the protection sleeve has to be stretched for removal of the hollow needle from the human or animal body which causes the operator to apply greater forces. Furthermore it is not guaranteed that the needle is pulled out perpendicular to the surface of the human or animal body, during removal of the needle from the human or animal body wherein an angular removal of the needle from the human or animal body can be painful for the patient. Furthermore due to the higher forces that are required to pull out the hollow needle from a human or animal body, the risk exists that the operating personal angularly shifts the upper housing and the connected needle from the puncture axis which is perpendicular to the surface of the human or animal body, and damages the protection sleeve between the upper housing and the lower cover plate.

SUMMARY

Therefore the present invention's objective is the manufacture of a safety needle device, in particular for puncturing of a in a human or animal body subcutaneously implanted port providing lower stresses for the patient during the insertion of a safety needle device into the port, during the application time of the safety needle device, and during removal of the safety needle device from the port.

The object is achieved by a safety needle device, particularly for the puncture of a port implanted subcutaneously in a human or animal body, comprising a first housing; a hollow needle, wherein the needle has a first sub-section and a second sub-section, and the first sub-section extends along a puncture axis, which runs at a right angle to the surface of the human or animal body, and the second sub-section of the needle being arranged at a right angle to the first sub-section, substantially in parallel to the surface of the human or animal body, wherein the hollow needle is or can be connected to the first housing, particularly in the region of the second sub-section; a cover comprising a through-hole for receiving the first sub-section of the needle, wherein the cover can be moved from a first position into a second position relative to the first housing, wherein the movement occurs substantially along the puncture axis; and an at least partially flexible limiting element for limiting the relative movement between the first housing and the cover in the second position, characterized in that the cover has, on the surface facing away from the human or animal body, a guide sleeve for the first sub-section of the needle.

For the insertion of the safety needle device according to the invention into a port implanted subcutaneously in a human or an animal body, the first housing and the cover are arranged directly adjacent to each other and are preferably releasably connected to each other. In this first position the first sub-section of the needle extends through the through-hole in the cover and continues into the direction of the puncture axis. In this first position the safety needle device can be inserted into a subcutaneously implanted port until the needle tip reaches the bottom of the port. In this implanted state the safety needle device according to the invention can be fixed relatively to the human or animal body, for example using adhesive tape or patches. In this implanted state especially the low construction height of the safety needle device according to the invention is advantageous, since thereby the wearing comfort for the patient is improved. According to an advantageous variant of the invention the safety needle device has a maximum height of 15 mm, preferably a maximum height of 10 mm.

For the removal of the safety needle device according to the invention from the port implanted subcutaneously, the medical personnel fixes the cover for example with one hand relatively to the human or animal body and moves the housing with the other hand relatively to the cover until the cover reaches the second position relatively to the first housing. In this second position the flexible limiting element, which is arranged between the first housing and the cover, restricts the relative movement between the first housing and the cover. In this second position the needle of the safety needle device is removed from the subcutaneously implanted port and the human or animal body, wherein the needle tip is preferably disposed within the guide sleeve. The relative movement between the cover and the first housing is determined by the guide sleeve, so that the needle is removed from the port in the direction of the puncture axis. Further, the needle tip is disposed within the guide sleeve in the second position, so that the needle tip is isolated from contact and the medical personnel cannot hurt themselves on the needle tip.

In the first position the flexible limiting element is disposed in a folded state between the first housing and the cover and is unfolded during the relative movement between first housing and the cover until a maximum extension is reached in the second position and limits the relative movement between the first housing and the cover.

Advantageously the tip of the needle is provided with a Huber-like sharpening. In an advantageous variant of the safety needle device according to the invention the first housing and the cover are arranged directly adjacent to each other in the first position, wherein in the first position the needle emerges from the human or animal body facing surface of the cover. In this first position the safety needle device according to the invention can be inserted in a simple manner in the subcutaneously implanted port of the human or animal body. According to a particularly advantageous variant of the safety needle device the first housing and the cover are fixable relatively to each other in the first position and/or in the second position, so that the insertion of the safety needle device according to the invention or the removal of the safety needle device from the port do not lead to a relative movement between a first housing and a cover.

In another variant the safety needle device according to the invention comprises a closure means for the through-hole in the cover which closes the through-hole for the needle in the second position. After the removal of the safety needle device according to the invention from the subcutaneously implanted port in the human or animal body, the cover of the safety needle device is located in a second position relatively to the first housing of the safety needle device and the tip of the hollow needle is arranged within the guide sleeve. To prevent the tip of the needle from emerging from the through-hole of the cover again, the through-hole is closed by closure means. Thereby the risk of injury to the medical personnel and the patient is further reduced.

In an advantageous variant of the safety needle device according to the invention the closure means is designed as a spring which is disposed in the first position between a surface of the cover, preferably a wall, and the needle and wherein the spring, when it reaches the second position in which the needle does not emerge from the through-hole of the cover, is unstressed and closes the through-hole for the needle. This ensures that the needle cannot emerge from the through-hole of the cover again after reaching the second position. Furthermore the spring which is designed as a closure means has the advantage that it rests in a first position against a shaft of the hollow needle in a stressed state and creates a holding force, whereby the cover is held relatively to the first housing.

Such a closure means designed as a spring comprises for example two legs and a winding area, wherein one leg rests against a surface of the cover and the other leg in the first position of the safety needle device rest against the first sub-section of the needle and in the second position of the safety needle device encloses the through-hole in the cover. The spring preferably consists of spring steel.

When reaching the second position, the first sub-section of the needle is removed from the through-hole of the cover and the spring is unstressed, so that a part of the spring rests against a further surface of the cover and closes the through-hole of the cover in this position. By unstressing the spring in the second position, a part of the spring moves against the surface of the cover, wherein the movement of the unstressing of the spring is limited in such a way that the through-hole in the cover is closed. When a part of the spring reaches the surface of the cover, an acoustic noise signal is created, which signals to the medical personnel that the closure means has closed the through-hole in the cover.

The closure means designed as a spring consists for example of spring steel and is formed from a wire like element having a diameter of 0.6 mm. The spring formed from spring steel has for example two legs each having a length of 6 mm and having 2.42 windings between the legs. An alternative spring is formed for example of a wire like element having a diameter of 0.5 mm, having two legs each with a length of 4 mm and having 0.92 windings between the two legs.

In an advantageous variant of the safety needle device according to the invention the cover has a fixing for the closure means to secure the closure means on the cover. The fixing is for example a cylindrical enhancement which engages in the winding of the spring. Alternatively or additionally, for example, cavities on the cover element may be provided, in which parts of the closure means, for example a leg of a spring, engage.

In an advantageous variant of the safety needle device according to the invention the limiting element is flexible and formed in such a way that the tip of the needle, which is arranged at the first sub-section of the needle, is arranged within the guide sleeve in the second position. In particular the flexible limiting element is formed such that the tip of the needle does not emerge from the guide sleeve in the direction of the first housing, but ensures at the same time that the through-hole in the cover can be closed for example by closure means in the second position. In such an embodiment of the flexible limiting element it is ensured that the tip of the needle is disposed in the second position in a normal use of the safety needle device according to the invention within the guide sleeve and that it is isolated from the contact with medical personnel or the patient.

According to a variant of the safety needle device according to the invention the limiting member is tubular and the first sub-section of the needle is at least partially disclosed within the tubular limiting element. In particular the shaft of the first sub-section of the hollow needle is disposed within the tubular limiting element in the second position and protects it from contact with the medical personnel or the patient.

In a particularly advantageous variant of the safety needle device according to the invention the tubular limiting element is conical, so that it can be folded together extremely flat in the first position, which in particular has a positive effect on the maximum construction height of the safety needle device according to the invention.

In an alternative embodiment of the safety needle device according to the invention the limiting element comprises at least one thread like or band-shaped element. A thread like or band-shaped element has the advantage that it can be stored in the first position consuming lesser space than a tubular limiting element. Although a thread like or band-shaped limiting element does not isolate the shaft of the first sub-section of the needle from contact with the medical personnel or the patient, no danger of injury from this shaft exists.

Advantageously the limiting element consists of a woven or braided material. In particular the limiting element may comprise a textile, a plastic or a metal.

According to a variant of the safety needle device according to the invention the limiting element is designed as a slotted strip, wherein the needle is arranged at least in the first position in the slotted portion of the band-shaped limiting element. In this example the limiting element may comprise hinges which are arranged in such a way that the limiting element is foldable in the first position substantially in parallel to the surface of the human or animal body. Such a limiting element has for example stiff segments, which are hinged together by means of film hinges so that the limiting element can be folded together flat in the first position and automatically unfolds at a relative movement in the second position. In order to place the limiting element as closed as possible to the needle of the safety needle device, the limiting element can comprise a slotted portion in which the needle is disposed at least in the first position.

In a preferred variant of the safety needle device according to the invention the cover has a cavity for receiving the limiting element in the first position. Thus the limiting element is protected by the cavity against external damages in the first position.

Advantageously the limiting element is attached to the first housing and/or the cover element, for example by an adhesive or clamp connection.

According to an advantageous variant of the inventive safety needle device, the first housing and/or the cover element comprises at least a wing, preferably two wings. The wings at the first housing and/or the cover element act as a handling aid of the safety needle device according to the invention during the insertion or the removal of the safety needle device in or from a port implanted subcutaneously in a human or animal body or as fixing means for fixing the safety needle device according to the invention relatively to the human or animal body in the inserted state.

In a particularly advantageous variant the at least one wing comprises a rib, which is intended to produce a feeling with maximum grip for the user of the safety needle device according to the invention and to avoid a slipping of one or more fingers of the operator during insertion or removal of the safety needle device according to the invention from or into the subcutaneously in the human or animal body implanted port.

According to an advantageous variant of the safety needle device according to the invention, two wings are arranged on the first housing and on the cover, wherein the wings at the first housing are preferably bigger or smaller than the wings at the cover. Therefore the wings can be preferably assigned to a first housing or a cover. In particular the wings at the first housing are formed bigger than the wings at the cover, since by mean of those the force is transmitted to the safety needle device according to the invention and used for removal of the needle from the port, while the wings of the cover serve only for fixing the cover relatively to the human or animal body and the subcutaneously implanted port catheter therein.

In a variant of the safety needle device according to the invention the wings are foldable from a first orientation which is substantially perpendicular to the puncture axis to a second orientation which is substantially parallel to the puncture axis. Thus, for example, the wings at a first housing can be folded into a second position, for removal of the needle from the subcutaneously in a human or animal body implanted port so that for removal of the needle a force along the puncture axis can be easily applied.

In an advantageous variant in first position, the surfaces of the wings which are facing away from the human or animal body, are arranged directly adjacent to each other in the second position, wherein the directly adjacent to each other arranged surfaces of the wings are preferably formed complementary to each other. This particularly improves the operating feeling during removal of the needle from the port, because the adjacent wings give the impression that it concerns a single element and the wings do not move relatively to each other.

In a particularly preferred variant of the safety needle device of the present invention, the first housing comprises at least one convexity, preferably two convexities for receiving of the operator fingers during the puncture of the implanted port. Advantageously the at least one convexity is arranged in the region of the puncture axis of the safety needle device according to the present invention.

The at least one convexity serves as a handling aid for the operating personnel during insertion of the needle into the subcutaneously in a human or animal body implanted port. Due to the arrangement of the at least one convexity in the area of the puncture axis, the safety needle device according to the invention can be placed exactly in the area of the port. The at least one convexity is, for example, arranged below the two foldable wings of the first housing, that are folded in parallel to the puncture axis during insertion or removal of the needle from the port and uncover the at least one convexity in this position.

According to a further advantageous variant of the safety needle device according to the invention the cover comprises sidewalls and a cap, which form a second housing together with the cover. This second housing, for example, protects the limiting element and/or the closure means against an external damage and/or contamination. Advantageously the cap of the second housing of the safety needle device according to the present invention provides a first opening for the needle, in particular for the first sub-section of the needle, and a second opening for the flexible limiting element.

According to another variant of the safety needle device according to the invention the needle has a length which is adapted to the, for example, subcutaneously in a human or animal body implanted port, wherein especially the length of the first sub-section of the needle is adapted to the port. Thus, it can be ensured, that the tip of the first sub-section of the needle reaches the bottom of the port and that the cover is arranged on the surfaces of the human or animal body to be fixed thereon. According to an advantageous variant the first housing and/or the cover and the port have a matching color marking. Thus the safety needle device which is suitable for a subcutaneously in a human or animal body implanted port can be selected in an easy way.

According to a further advantageous variant of a safety needle device according to the invention the cover and/or the first housing is at least partially transparent, in particular such that a puncture spot in the human or animal body and the subcutaneously implanted port therein are visible during the puncture for the operating personnel. Thus, the safety needle device according to the invention can be placed more accurately and can be inserted into the subcutaneously implanted port.

Advantageously a safety needle device according to the present invention is manufactured with at least one wing at the first housing and/or at a cover with at least one wing in the first position, so that the at least one wing of the safety needle device according to the present invention does not automatically collapse in direction of the puncture axis in the inserted state. This enables the security needle device according to the present invention to be attached at the surface of the human or animal body more easily.

The invention will become more apparent from the following detailed description in conjunction with the accompanying drawings.

BRIEF DESCRIPTION OF THE DRAWINGS

FIG. 9 shows a perspective view of a forth embodiment of a security needle device according to the invention in the first position, FIG. 10 is a perspective view of the safety needle device according to the invention on FIG. 9 in the second position.

DETAILED DESCRIPTION

Figure 1:
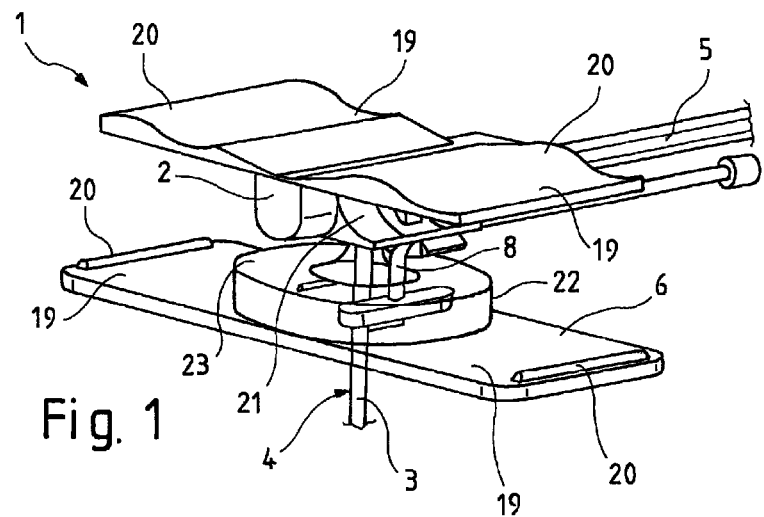
FIG. 1 is a perspective view of a first embodiment of a safety needle device according of FIG. 1 to the invention in a first position.

FIG. 1 shows a perspective view of a first embodiment of the inventive safety needle device 1 particularly for the puncture of a port implanted subcutaneously in a human or animal body, depicted in a first position. The inventive safety needle device 1 comprises a first housing 2 and a hollow needle 3, wherein the needle 3 comprises a first sub-section 4 and a second sub-section 5, wherein the first sub-section 4 extends along a puncture axis, which runs at a right angle to the surface of the human or animal body and the second sub-section 5 of the needle 3 being arranged at a right angle to the first sub-section 4, substantially in parallel to the surface of the human or animal body, wherein the hollow needle 3 is or can be connected to the first housing 2, particularly in the region of the second sub-section 5. The inventive safety needle device 1 according to FIG. 1 further comprises a cover 6 with a through-hole 7 for receiving the first sub-section 4 of needle 3, wherein the cover 6 is moveable from a first position to a second position relatively to the first housing 2, wherein the movement occurs substantially along the puncture axis. The inventive safety needle device 1 from FIG. 1 further comprises an at least partially flexible limiting element 8, for limiting the relative movement between the first housing 2 and the cover 6 in the second position. The cover 6 has a guide sleeve 9 for the first sub-section 5 of the needle 3 on the surface averted from the human or animal body.

In the first position the first housing 2 and the cover 6 are arranged directly adjacent to each other, wherein the tip of the needle 3 in the first position emerges from the surface of the cover facing the human or animal body. In this first position the depicted inventive safety needle device is inserted into a port implanted subcutaneously in a human or animal body.

The inventive safety needle device 1 can be fixed relatively to the human or animal body in the inserted state, for example by fixation of the inventive safety needle device on the surface of the human or animal body with plaster. In the first position depicted in FIG. 1 the first housing 2 and the cover 6 are fixed relatively to each other, as described below in more detail.

For closure of the through-hole 7 in the second position the inventive safety needle device 1 further comprises a closure means 10 for the through-hole 7 in cover 6. The closure means 10 is, for example, designed as a string 12, which is arranged in the first position between a surface of the cover 6, preferably a wall 11 and the needle 3, and wherein the spring 12 is unstressed on reaching the second position, in which the needle 3 does not emerge from the through-hole 7 in the cover 6, and closes the through-hole 7 for the needle 3. In the first position the spring 12 is stressed between the wall 11 of the cover 6 and the shaft of the first sub-section 4 of the needle 3, which leads to a friction between the shaft of the needle 3 and the spring 12. Due to this friction the first housing 2 is fixed relatively to the cover 6. By applying an external force through an operator the inventive safety needle device 1 depicted in FIG. 1 can be transferred from a first position to a second position which is depicted in FIG. 2, leading the needle 3 to be pulled out of the port and the human or animal body.

Figure 2:
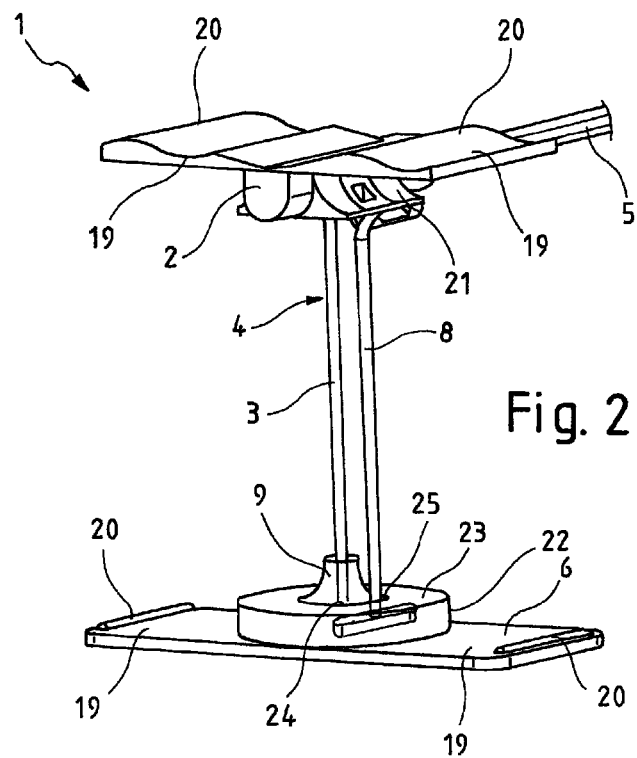
FIG. 2 is a perspective view of the safety needle device according to the invention in a second position.

FIG. 2 depicts the limiting element 8 in a position which limits the relative movement between the first housing 2 and the cover 6. In this second position the tip of the needle 3 is arranged within the guide sleeve 9 of cover 6 and is isolated from a contact with the operator or the human or animal body of the patient.

The closure means 10 designed as a spring 12 comprises two legs 13 and a winding 14 wherein one leg 13 rests against a surface of cover 6 and the other leg 13 rests against the first sub-section 4 of needle 3 in the first position of the inventive safety needle device 1 and closes the through-hole 7 in the cover 6 in the second position of the inventive safety needle device 1. This ensures that the tip of the needle 3 cannot emerge from the through-hole 7 in cover 6 after reaching the second position again, which significantly increases the safety of the inventive safety needle device 1.

The cover element 6 of the inventive safety needle device 1 depicted in FIGS. 1 and 2 further has a fixing 15 for the closure means 10. For fixing the closure means 10 to the cover 6 the fixing 15 engages in the winding 14 of the spring 12 for example in form of a cylindrical enhancement.

The flexible limiting element 8 of the inventive safety needle device 1 is designed such that the tip of the needle 3 in the second position is arranged within the guide sleeve 9. In particular the flexible limiting element 8 has a lower elasticity, so that even upon application of a greater force the tip of the needle 3 remains at all times in the guide sleeve 9 of the cover 6. The limiting element 8 of the inventive safety needle device 1 depicted in FIGS. 1 and 2 has a round diameter and consists for example of plastic. Alternatively the limiting element 8 can be also formed of a thread like element, which consists for example of a woven or braided material, in particular a textile, a plastic or a metal. The limiting element 8 is fixed to the cover 6 and to the first housing 2 in a guiding, wherein the guiding and the limiting element 8 are designed such that the relative movement between the first housing 2 and the cover 6 is limited in the second position.

The first housing 2 and the cover 6 of the inventive safety needle device 1 depicted in FIGS. 1 and 2 comprise each two wings 19 for better handling of the inventive safety needle device 1 during insertion or removal of the inventive safety needle device 1 in or from the subcutaneously in a human or animal body implanted port. The wings 19 of the first housing 2 and the cover 6 comprise each a rib for a handling with maximum grip for the user.

The wings 19 of the first housing 2 are foldable from a first orientation, which is substantially perpendicular to the puncture axis, to a second orientation, which is substantially parallel to the puncture access. In the second orientation the surfaces of the wings 19, which are opposite of the human or animal body in the first orientation, are arranged adjacent to each other, wherein the adjacent to each other arranged surfaces of the wings 19 are preferably complementary to each other.

The first housing 2 further has two convexities 21 for receiving fingers of the operating personnel during the puncture of the in a human or animal implanted port. The convexities 21 are arranged below the foldable wings 19 of the first housing 2 in the area of the puncture axis and are accessible for the operating personnel after folding of the wings 19 to the second orientation.

The cover 6 further comprises side walls 22 and a cap 23 which form a second housing together with the cover 6. The cap 23 of the second housing has a first opening 24 for the needle 3 and a second opening 25 for the flexible limiting element 8. The needle 3 of the inventive safety needle device 1 depicted in FIGS. 1 and 2 has preferably a length which is adapted to the subcutaneously in a human or animal body implanted port. Expediently the first housing 2 and/or the cover 6 of the inventive safety needle device 1 depicted in FIGS. 1 and 2 and the subcutaneously in a human or animal body implanted port have a matching color marking.

According to a further advantageous embodiment of the inventive safety needle device 1 the cover 6 and/or the housing 2 are at least partially transparent, in particular such that the injection spot is visible for the operating personnel during the puncture of the port. The second sub-section 5 of the needle 3 may end within the first housing 2 and can be connected there with a feedline or can leave the first housing 2 perpendicularly to the puncture axis and can be subsequently connected to a feedline.

Figure 3:
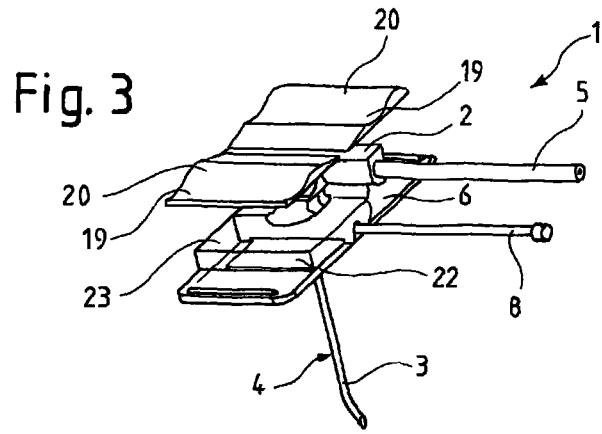
FIG. 3 shows a perspective view of a second embodiment of a safety needle device according to the invention in the first position.
Figure 4:
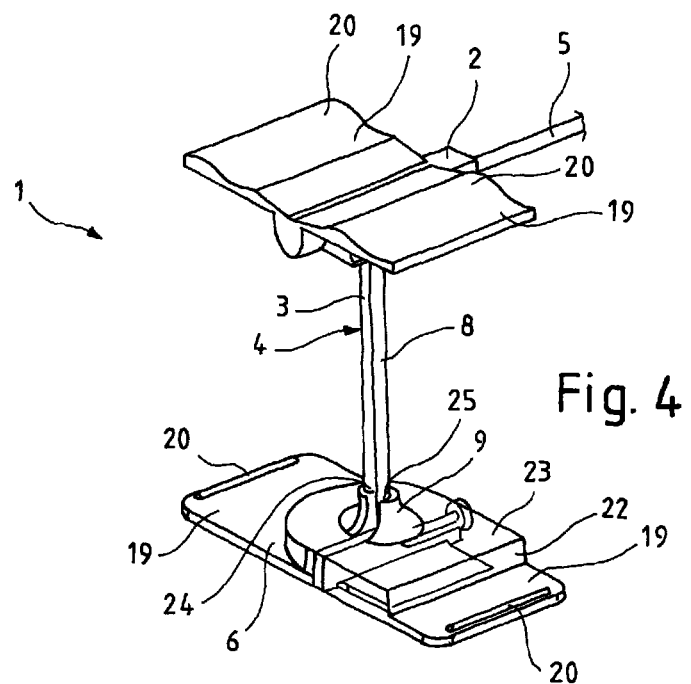
FIG. 4 shows a perspective view of the safety needle device according to the invention of FIG. 3 in the second position.

FIG. 3 shows a perspective view of a second embodiment of an inventive safety needle device 1 in the first position and FIG. 2 shows a perspective view of the safety needle device 2 from FIG. 3 in the second position. The second embodiment of the inventive safety needle device 1 according to FIGS. 3 and 4 differs from the first embodiment of the inventive safety needle device 1 according to FIGS. 1 and 2 in that the limiting element 8 is being fixedly connected to the first housing 2 and being kept in guiding arranged in the area of cover 6. The limiting element 8 and the guiding are designed such that the relative movement between the first housing 2 and the cover 6 in the second position is limited. The guiding of the limiting element 8 in the area of cover 6 guides the limiting element 8 out of the second housing, which is formed by cover 6, side walls 22 and cap 23. The rest of the second embodiment depicted in FIGS. 3 and 4 matches with the first embodiment according to FIGS. 1 and 2.

Figure 5:
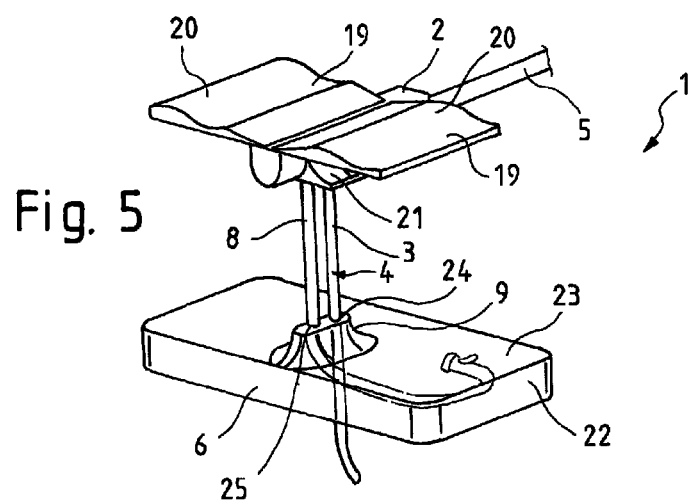
FIG. 5 shows a perspective view of a third embodiment of a safety needle device according to the invention in an intermediate position.

FIG. 5 shows a perspective view of a third embodiment of an inventive safety needle device 1 in an intermediate position. The third embodiment according to FIG. 5 differs from the second embodiment according to FIGS. 3 and 4 in that the limiting element 8 is guided inside the cover 6 which is designed as a second housing and is not guided laterally outwards according to the second embodiment of the inventive safety needle device 1 according to FIGS. 3 and 4. The cover 6 of the inventive safety needle device 1 from FIG. 5 has a cavity 18, which serve for receiving the limiting element 8 in the first position. During the transmission from the first position to the second position the limiting element 8 is pulled out of the cavity 18 continuously via the second through-hole 7 in cap 23 of the second housing, until it limits the relative movement between the first housing 2 and the cover 6 in the second position and cannot be further pulled out of the opening 22 in cap 23.

Figure 6:
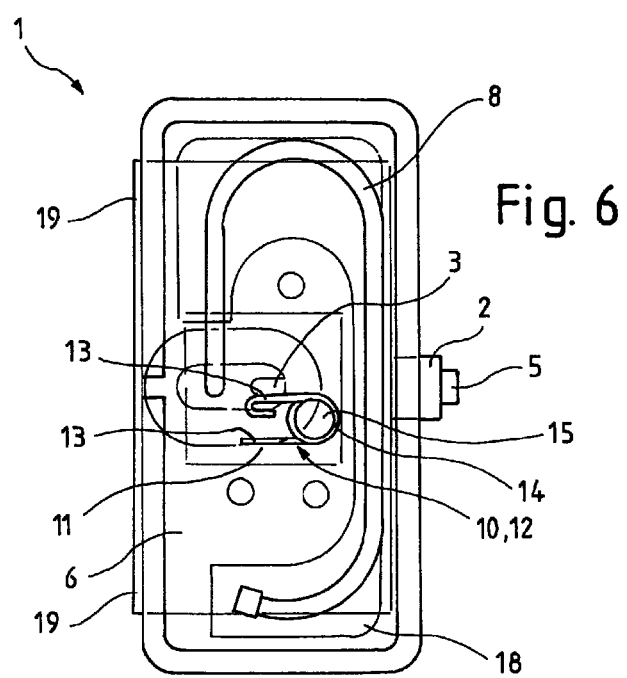
FIG. 6 shows a view from the human or animal body-facing side of the inventive safety needle device of FIG. 5 in the first position.

FIG. 6 shows a view of the side facing the human or animal body on the inventive safety needle device 1 from FIG. 5 in the first position. In this first position the limiting element 8 is arranged inside the cavity 18 of cover 6. Furthermore FIG. 6 displays the spring 12 which forms a closure means 10. The spring 12 has two legs 13 and one winding 14. In the depicted first position the spring 12 is stressed between a wall 11 of the cover 6 and the shaft of the first sub-section 4 of the needle 3 and is additionally fixed with fixing 15 at cover 6. The fixing 15 has the form of a cylindrical enhancement which engages in the winding 14 of the spring 12.

Figure 7:
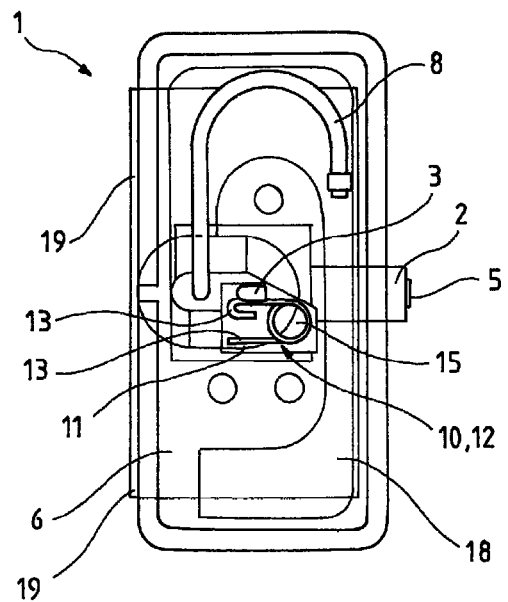
FIG. 7 shows a view from the human or animal body-facing side of the inventive safety needle device of FIG. 5 in the intermediate position.

FIG. 7 shows a view of the side facing the human or animal body to the inventive safety needle device 1 from FIG. 5 in the intermediate position. In this intermediate position the limiting element 8 has been pulled out of the cover 6 partially as the first housing 2 has been removed from the cover 6. Simultaneously the needle 3 has been partially pulled out of the subcutaneously in a human or animal body implanted port.

Figure 8:
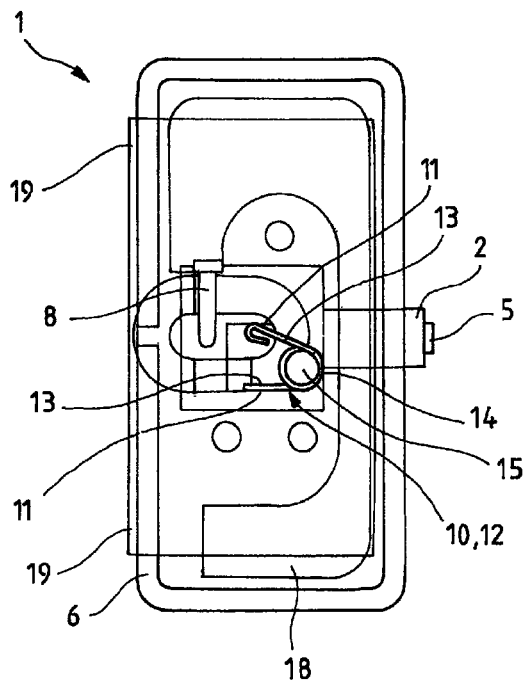
FIG. 8 is a view of the human or animal body-facing side of the inventive safety needle device of FIG. 5 in the second position.

FIG. 8 shows a view from the side facing the human or animal body of the inventive safety needle device 1 from FIG. 5 in the second position. In the second position the limiting element 8 limits the relative movement between the first housing 2 and the cover 6 of the inventive safety needle device 1. In this second position the end of needle 3 is arranged inside the sleeve 9 of cover 6 and does not emerge from the through-hole 7 in cover 6. The closure means 11 designed as a spring 12 closes the through-hole 7 with a leg 13 in this second position as the spring 12 has unstressed after removal of needle 3 from the through-hole 7 until reaching the wall 11 of cover 6, wherein the end of leg 13 is formed in such a way that it closes the through-hole 7 in cover 6 for needle 3.

FIG. 9 shows a perspective view of a fourth embodiment of an inventive safety needle device 1 in the first position and FIG. 10 shows a perspective view of an inventive safety needle device 1 from FIG. 9 in the second position. The fourth embodiment according FIGS. 9 and 10 differs from the first embodiment according FIGS. 1 and 2 in that the limiting element 8 is a flexible band which, for example, consists of plastic and has a rectangular cross-section. Alternatively the limiting element 8 can also consist of a woven or braided material, for example by using textile, plastic or metal.

The limiting element 8 is fixed at the cover 6 and at the first housing 2 and limits in the second position, which is depicted in FIG. 10, the relative movement between the first housing 2 and the cover 6 in such a way that the tip of the needle 3 is arranged inside the guide sleeve 9 of cover 6.

Figure 11:
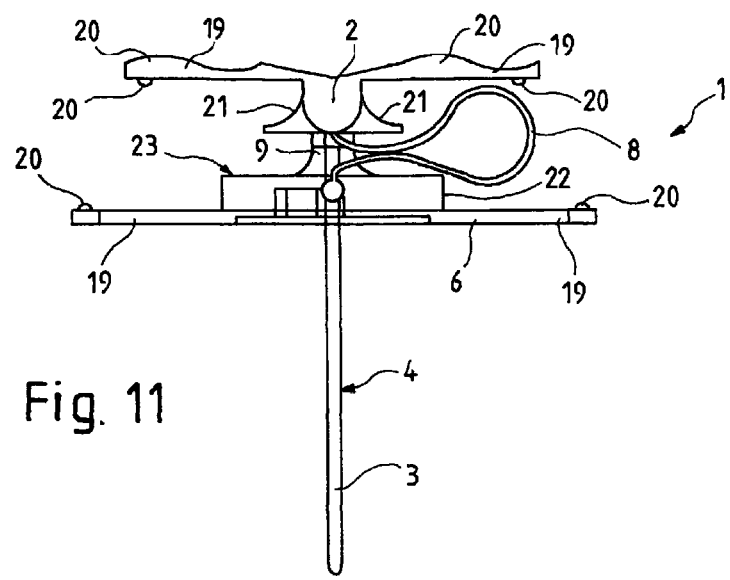
FIG. 11 is a side view of a fifth embodiment of a safety needle device according to the invention in the first position.
Figure 12:
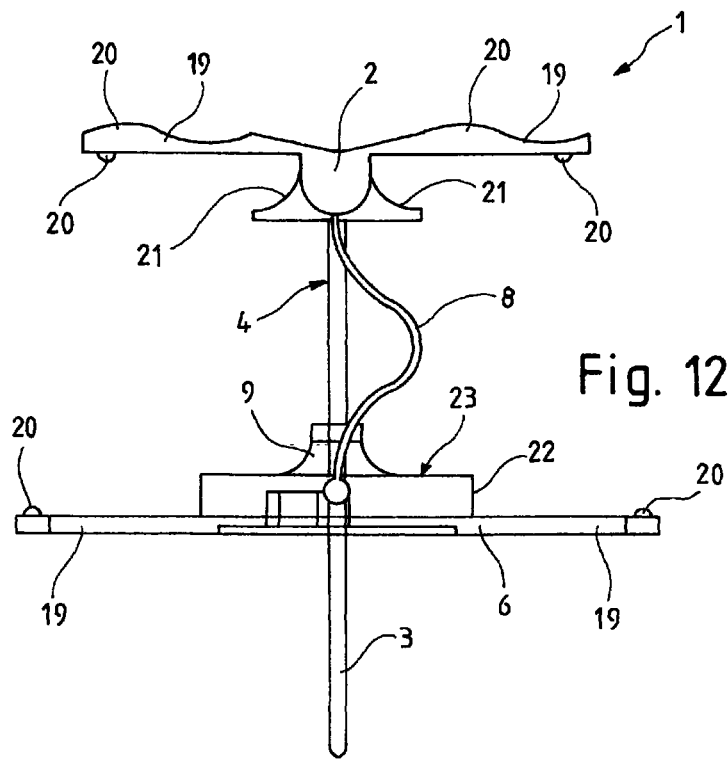
FIG. 12 is a side view of the safety needle device according to the invention of FIG. 11 in the intermediate position.
Figure 13:
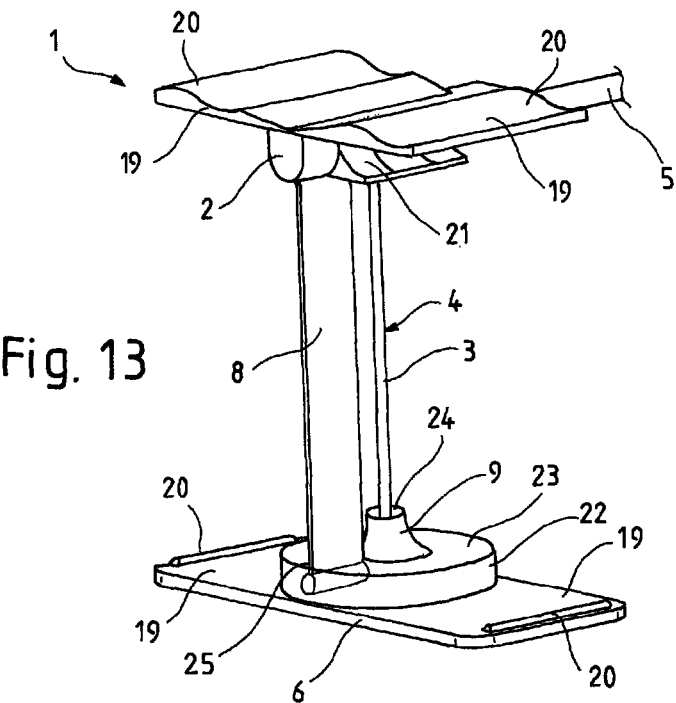
FIG. 13 is a perspective view of the safety needle device according to the invention of FIG. 11 in the second position.

FIG. 11 shows a side view of a fifth embodiment of an inventive safety needle device 1 in the first position, FIG. 12 shows a side view of the inventive safety needle device 1 from FIG. 11 in an intermediate position and FIG. 13 shows a perspective view of the inventive safety needle device 1 from FIG. 11 in the second position. The fifth embodiment according FIGS. 11 to 13 differs from the fourth embodiment according FIGS. 9 and 10 with respect to the guiding of the flexible limiting element 8. In the fourth embodiment according to FIGS. 9 and 10 the flexible limiting element 8 is folded up in the first position in direction of the second sub-section 5 of needle 3 respectively the feedline to the first housing 2, whereas the flexible limiting element 8 according to the fifth embodiment in FIGS. 11 to 13 is folded up below the wings 10 of the first housing 2 of the inventive safety needle device 1. Furthermore, the limiting element 8 is fixed at the border of cover 6 outside the second housing in the fourth embodiment according to FIGS. 9 and 10, whereas the limiting element 8 is fixed inside the housing of cover 6 and emerges through a second opening 25 in cap 23 of the second housing in the fifth embodiment according to FIGS. 11 to 13.

Figure 14:
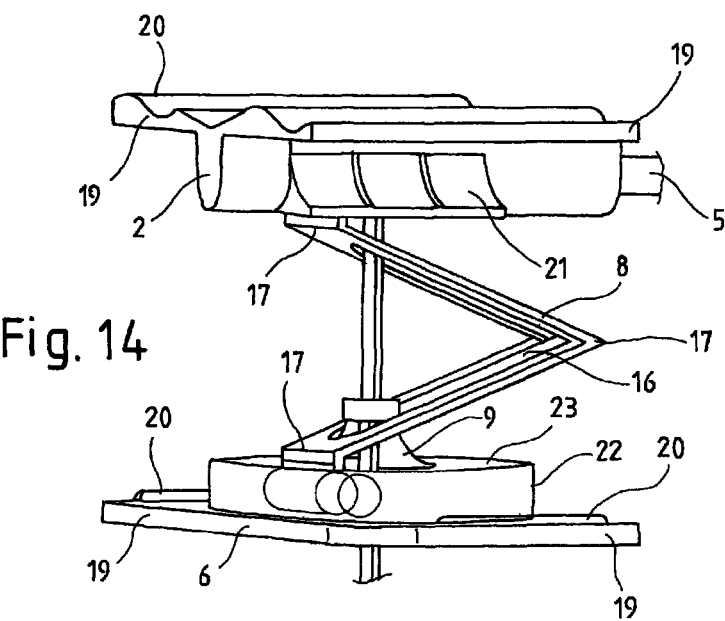
FIG. 14 is a perspective view of a sixth embodiment of a safety needle device according to the invention in the intermediate position.
Figure 15:
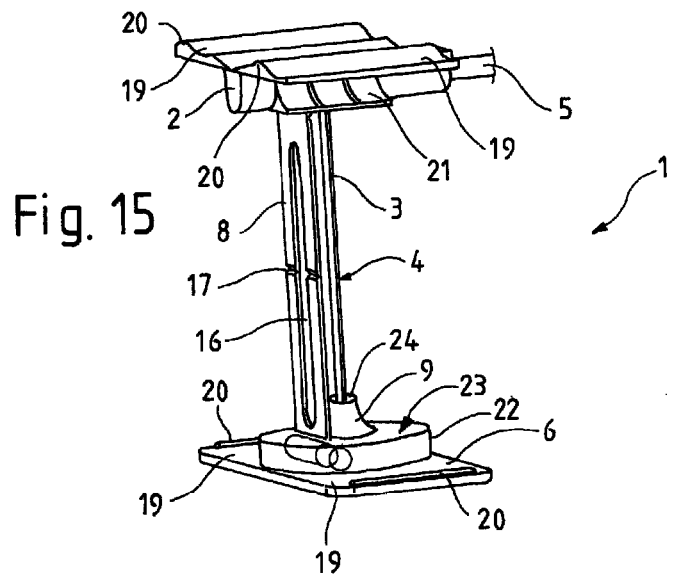
FIG. 15 is a perspective view of the inventive safety needle device of FIG. 14 in the second position.

FIG. 14 shows a perspective view of a sixth embodiment of an inventive safety needle device 1 in the intermediate position. FIG. 15 shows a perspective view of the inventive safety needle device 1 from FIG. 14 in the second position. The sixth embodiment according FIGS. 14 and 15 differs from the fourth embodiment of the inventive safety needle device 1 from FIGS. 9 and 10 in that the limiting element 8 has two stiff segments which are arranged between three film hinges in a fitting way. Furthermore the limiting element 8 comprises a slotted portion 16 in which the first sub-section 4 of the needle 3 is arranged in at least the first position, preferably also during the relative movement between the first housing 2 and the cover 6 until the second position is reached. In the first position the limiting element 8 is arranged substantially parallel to the surface of the human or animal body. Furthermore, the limiting element 8 is arranged inside the second housing of covers 6 like in the fifth embodiment according to FIGS. 11 and 12.

Figure 16:
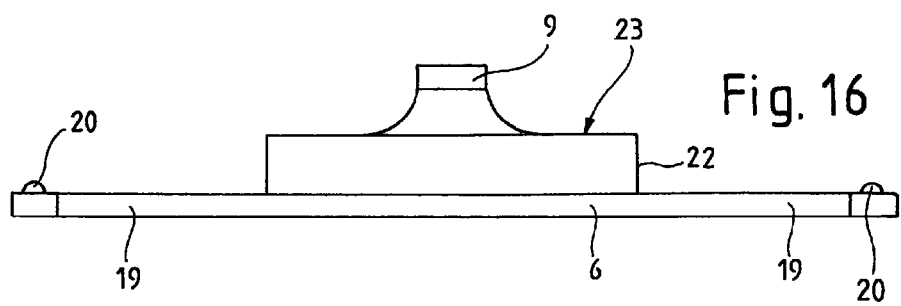
FIG. 16 is a detailed side view of a cover of an inventive safety needle device.
Figure 17:
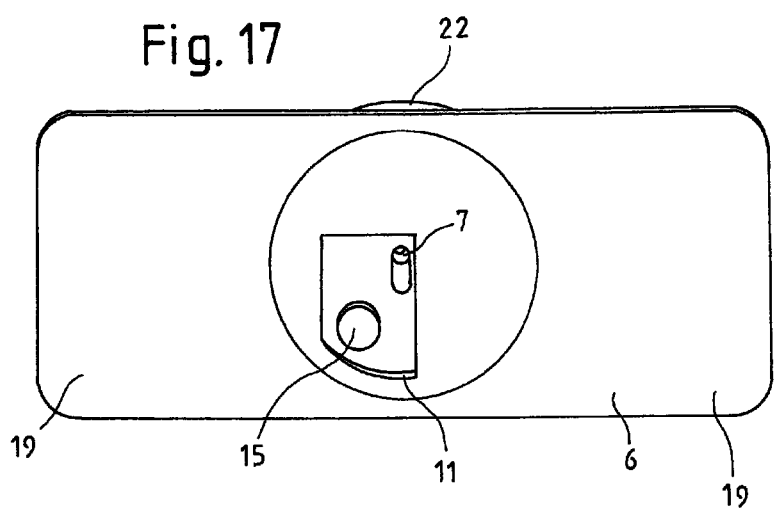
FIG. 17 shows a detailed view of the human or animal body-facing side of the cover of FIG. 16.

FIG. 16 shows a detailed side view of a cover 6 of an inventive safety needle device 1. FIG. 17 shows a detailed view of the side facing the human or animal body to cover 6 from FIG. 16. FIG. 17 particularly shows that cover 6 comprises a cavity with side walls 11, in which the closure means 10 can be arranged. Furthermore a fixing 15 for the closure means, which is designed as a cylindrical enhancement, is arranged inside the cavity.

Figure 18:
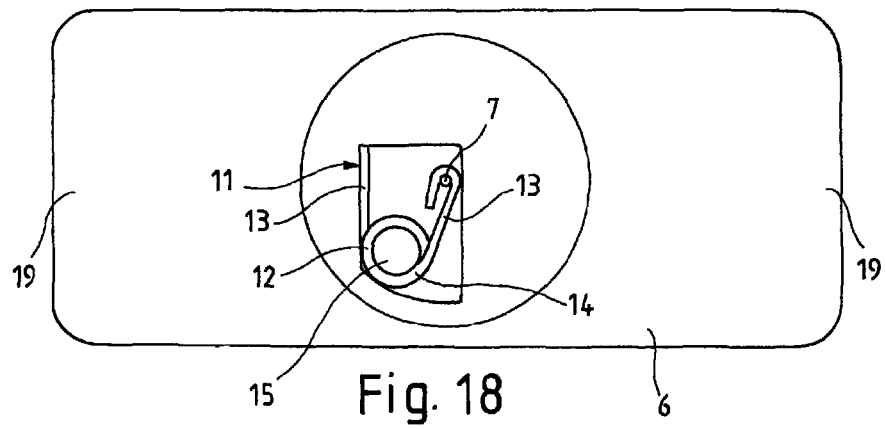
FIG. 18 is a detailed view according to FIG. 17 with closure means arranged in the cover.

FIG. 18 shows a detailed view of a cover 6 according to FIG. 17 with closure means 10 arranged in the cover 6. The closure means 10 is designed as a spring 12 and comprises two legs 13 and one winding 14, wherein the cylindrical enhancement 15 engages in the winding 14 of the spring 12. FIG. 18 shows the cover 6 in the second position, in which one leg 13 of the spring 12 closes the through-hole 7 in cover 6 for the needle 3.

Figure 19:
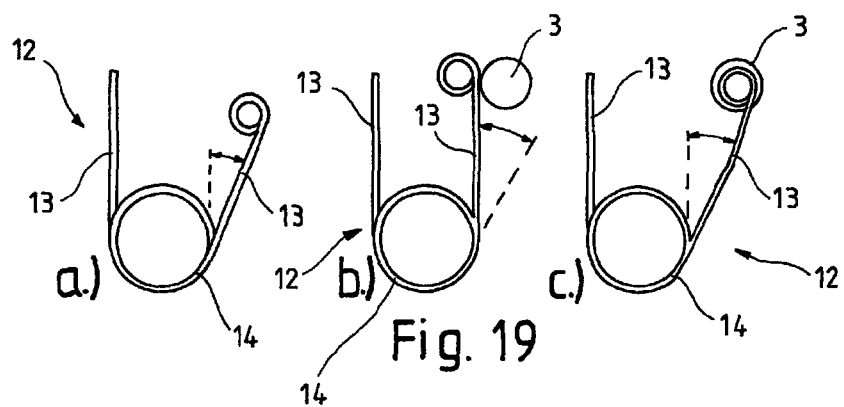
FIG. 19 shows detailed views of closure means designed as a spring for the use with a safety needle device according to the invention.

FIG. 19 shows a detailed view of a closure means 10, designed as a spring 12, for the use with an inventive safety needle device 1. FIG. 19a shows the spring 12 in an unstressed state. Thereby the legs 13 of needle 12 have a length of 6 mm. In the area of the through-hole 7 of cover 6 one leg 13 has a further winding to close the through-hole 7 for needle 3. The winding area 14 of the spring 12 has for example 2.42 windings and an inner diameter of 4 mm. FIG. 19b shows the spring 12 in the first position of the safety needle device 1. In this first position one leg 13 of the spring 12 rests against the shaft of the first sub-section 4 of needle 3 in such a way, that the spring 11 is in a stressed state. In this stressed state a friction is created between leg 13 and the shaft of needle 3, whereby, for example, a relative movement between the first housing 2 and a cover 6 of the inventive safety needle device 1 is avoided.

FIG. 19c shows the spring 12 in the second position of the inventive safety needle device 1. In this second position both legs 13 rests against the spring 12 at a side wall of cover 6, wherein spring 12 is in a slightly stressed state and one leg 13 closes the through-hole 7 in cover 6 for needle 3.

Figure 20:
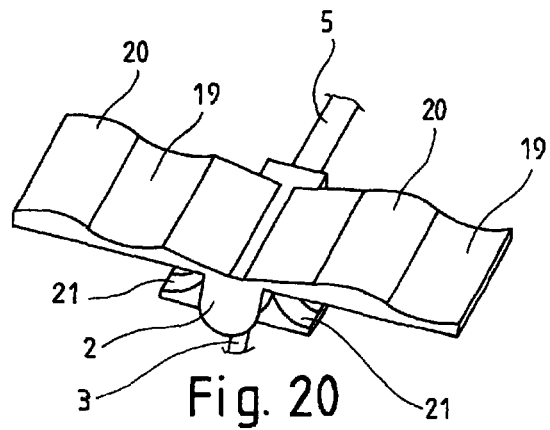
FIG. 20 shows a detailed view of a first housing of the inventive safety needle device.

FIG. 20 shows a detailed view of a first housing 2 of an inventive safety needle device 1. FIG. 20 particularly shows the convexities 21 for the fingers of an operator, which are arranged below the wings 19. Furthermore, FIG. 20 shows the surfaces of the wings 19 which are complementary to each other. The complementary to each other designed surfaces of the wings 19 are arranged on the surface facing away from the human or animal body in the first position and engage into each other, when the wings 19 are folded together.

Figure 21:
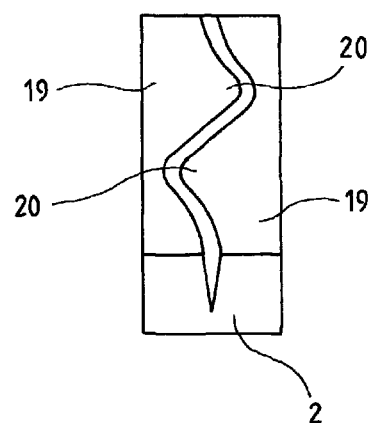
FIG. 21 is a sectional view of folded wings of a first housing of a safety needle device according to the invention.

FIG. 21 shows a sectional view of the folded wings 19 of a first housing 2 of an inventive safety needle device 1. In this position the surfaces of the wings 19 which are designed complementary to each other engage into each other so that the operating personnel perceives the feeling that it is one single element, which enhances the usage of an inventive safety needle device 1.

REFERENCE LIST 1 safety needle device
2 first housing
3 hollow needle
4 first sub-section
5 second sub-section
6 cover
7 through-hole
8 limiting element
9 guide sleeve
10 closure means
11 wall of cover
12 spring
13 leg
14 winding area
15 fixing
16 slotted portion of limiting element 17 film hinges
18 cavity of cover
19 wings
20 rib
21 convexity for fingers
22 side walls
23 cap
24 first opening in cap
25 second opening in cap

What is claimed is:

1. A safety needle device, particularly for the puncture of a port implanted subcutaneously in a human or animal body, comprising:
    a first housing;
    a hollow needle, wherein the needle has a first sub-section and a second sub-section, and the first sub-section extends along a puncture axis, which runs at a right angle to the surface of the human or animal body, and the second sub-section of the needle being arranged at a right angle to the first sub-section, substantially in parallel to the surface of the human or animal body, wherein the hollow needle is or can be connected to the first housing, particularly in the region of the second sub-section;
    a cover comprising a through-hole for receiving the first sub-section of the needle and, on a surface facing away from the human or animal body, a guide sleeve configured to guide movement of the first sub-section of the needle;
    wherein the first housing and the cover are transitionable from a first position relative to one another into a second position relative to one another with movement of the first sub-section of the needle;
    wherein the guide sleeve guides the movement of the first sub-section of the needle substantially along the puncture axis such that the first sub-section of the needle remains on the puncture axis when the first housing and the cover transition from the first position to the second position; and
    an at least partially flexible limiting element which limits the relative movement between the first housing and the cover in the second position; and
    wherein the second position corresponds to a position of maximum extension of the limiting element.

2. The safety needle device according to claim 1, wherein the first housing and the cover in the first position are arranged directly adjacent to each other, wherein the tip of the needle in the first position emerges from the surface of the cover facing the human or animal body.

3. The safety needle device according to claim 1, wherein the first housing and the cover in the first position and/or the second position are fixable relative to each other.

4. The safety needle device according to claim 1, wherein the safety needle device further comprises a closure means for the through-hole in the cover which closes the through-hole for the needle in the second position.

5. The safety needle device according to claim 4, wherein the closure means is designed as a spring which is arranged in the first position between a surface of the cover and the needle, and wherein the spring is unstressed on reaching the second position, in which the needle does not emerge from the through-hole in the cover, and closes the through-hole for the needle.

6. The safety needle device according to claim 5, wherein the spring comprises two legs and a winding section, wherein one leg rests against a surface of the cover and the other leg in the first position of the safety needle device rests against the first sub-section of the needle and closes the through-hole in the cover in the second position of the safety needle device.

7. The safety needle device according to claim 5, wherein the cover element has a fixing for the closure means for fixing the closure means to the cover.

8. The safety needle device according to claim 1, wherein the flexible limiting element is formed in such a way that the tip of the needle in the second position is arranged within the guide sleeve.

9. The safety needle device according to claim 8, wherein the limiting element is tubular and the first sub-section of the needle is at least partially arranged within the tubular limiting element.

10. The safety needle device according to claim 9, wherein the tubular limiting element is conical.

11. The safety needle device according to claim 8, wherein the limiting element comprises at least one thread-like or band-shaped element.

12. The safety needle device according to claim 11, wherein the limiting element consists of a woven or braided material.

13. The safety needle device according to claim 11, wherein the limiting element is designed as a slotted strip, wherein the needle is arranged at least in the first position in a slotted portion of the band-shaped limiting element.

14. The safety needle device according to claim 1, wherein the limiting element consists of a textile, a plastic or a metal.

15. The safety needle device according to claim 13, wherein the limiting element comprises film hinges which are arranged in such a way that the limiting element is foldable in the first position substantially in parallel to the surface of the human or animal body.

16. The safety device according to claim 1, wherein the cover has a cavity for receiving the limiting element in the first position.

17. The safety needle device according to claim 1, wherein the limiting element is attached on the first housing and/or the cover.

18. The safety needle device according to claim 1, wherein the first housing and/or the cover comprises at least one wing.

19. The safety needle device according to claim 18, wherein the at least one wing has at least one rib.

20. The safety needle device according to claim 18, wherein the at least one wing on the housing and/or the cover comprises at least two wings arranged on the first housing and at least two wings arranged on the cover.

21. The safety needle device according to claim 18, wherein the at least one wing on the housing and/or the cover comprises at least two wings, wherein the two wings are foldable from a first orientation, which is substantially perpendicular to the puncture axis, to a second orientation substantially in parallel to the puncture axis.

22. The safety needle device according to claim 21, wherein the at least one wing on the housing and/or the cover comprises at least two wings, wherein surfaces of the wings that are facing away from the human or animal body in the first orientation are arranged directly adjacent to each other in the second orientation.

23. The safety needle device according to claim 1, wherein the first housing comprises at least one convexity for receiving of the operator's fingers during the puncture of the implanted port.

24. The safety needle device according to claim 23, wherein the convexity is arranged in the region of the axis of the puncture.

25. The safety needle device according to claim 1, wherein the cover has side walls and a cap, which form a second housing together with the cover.

26. The safety needle device according to claim 25, wherein the cap has a first opening for the needle and/or a second opening for the flexible limiting element.

27. The safety needle device according to claim 1, wherein the needle has a length which is adapted to the subcutaneously implanted port catheter.

28. The safety needle device according to claim 27, wherein the first housing and/or the cover and the port having a matching color marking.

29. The safety needle device according to claim 1, wherein the cover and/or the first housing is at least partially transparent.

\* \* \* \* \*